United States Patent [19]

McCarthy

[11] Patent Number: 4,765,007

[45] Date of Patent: Aug. 23, 1988

[54] LEAF CUTTER BEE NEST BLOCK

[76] Inventor: Grant R. McCarthy, 12150 160 Street, Edmonton, Alberta, Canada, T5V 1H5

[21] Appl. No.: 459

[22] Filed: Jan. 5, 1987

[51] Int. Cl.⁴ ............................................. A01K 47/00
[52] U.S. Cl. ...................................................... 6/1
[58] Field of Search ........................................ 6/1, 11

[56] References Cited

U.S. PATENT DOCUMENTS

| | | | |
|---|---|---|---|
| 2,561,147 | 5/1947 | Smith | 6/11 |
| 3,105,978 | 7/1961 | Krekel | 6/11 |
| 3,191,199 | 6/1965 | Barnes, Jr. | 6/11 |
| 3,267,497 | 12/1964 | Dority | 6/11 |
| 3,936,894 | 2/1976 | Barber | 6/11 |
| 4,491,994 | 1/1985 | Youssef | 6/1 |
| 4,628,558 | 12/1986 | Pederson | 6/1 |
| 4,651,372 | 3/1987 | Schmidt | 6/11 |

FOREIGN PATENT DOCUMENTS 974817  9/1975  Canada .

Primary Examiner—Robert P. Swiatek
Attorney, Agent, or Firm—Hugh O'Gorman; Russel S. Smart; Stewart L. Gitler

[57] ABSTRACT

A unique mixture of expanded polystyrene beads and vermiculite is molded to form a one piece nesting block, having a plurality of egg laying holes for the leaf cutter bee. The unique nesting block is light weight and possesses the necessary environmental characteristics attractive to the leaf cutter bee namely, dissipation of water while providing a degree of permeability necessary to prevent mold and other harmful effects to the bee larvae.

3 Claims, 4 Drawing Sheets

LEAF CUTTER BEE NEST BLOCK

DESCRIPTION OF THE INVENTION

This invention relates to nesting blocks for bees and more particular, a nesting block for the leaf cutter bee.

BACKGROUND OF THE INVENTION

In areas where alfalfa and other crops are grown, it is known that pollination greatly improves the yield. Honey bees, wasps, and other insects have been found to pollinate crops, but it is the leaf cutter bee which is one of the superior pollinaters. Unfortunately, the leaf cutter bee does not fly far from its nesting site. As such, it is necessary to bring the nesting site closer to the areas to be pollinated.

In nature, the leaf cutter bee finds a crevice or hole in a tree or log and lays its eggs therein, sealing the opening of the hole with a small piece of cut leaf. The cut leaf discourages other leaf cutter bees from entering and laying eggs in the same hole, and also prevents parasites and other intruders from entering the hole.

PRIOR ART

It is known in the art to simulate the natural nesting habitat of the leaf-cutter bee by using a block of wood with holes bored therein as an artificial nesting site. These nest blocks, once filled with eggs, are moved into the fields where pollination is required. Once the young bees hatch they restrict their area of pollination and travel to the new nesting site. The wooden blocks are expensive to produce, heavy, and difficult to clean.

A multiplicity of thin wooden boards having parallel grooves on one face from edge to edge have also been used. Such a device is disclosed in U.S. Pat. No. 3,936,894. This device allows the larvae to be viewed and the nesting holes to be cleaned.

A disposable type of nesting device has also been used. It is cheaper, more economical, and easier to handle. Boards similar to those described in U.S. Pat. No. 3,936,894 are made of expanded polystyrene beads and placed together.

Finally the inventor of the present invention made and used a one piece nesting block constructed out of expanded polystyrene beads, with a plurality of holes molded therein. It has been found, however, that there is not a sufficient amount of permeability of moisture travel through the expanded polystyrene block, and that mold and other damage occurs with loss of the larvae.

It is therefore an object of the present invention to construct a one piece nesting block with the desired characteristics of both environmental water dissipation and permeability of air and moisture through the construction. It has now been discovered that a mixture of vermiculite and expanded polystyrene beads offers the desirable properties.

SUMMARY OF THE INVENTION

Therefore, this invention provides for a one piece molded nesting block for leaf cutter bees comprising a mixture of at least one permeable substance and expanded polystyrene beads, including a plurality of bore holes formed therethrough, said bore holes being of sufficient diameter for a leaf cutter bee to pass therein.

In another embodiment of the invention, one end of a certain number of said bore holes are molded closed such that in operation when a backing sheet is applied to one side of said nesting block said molded closed holes are inaccessible to bees.

In a preferred embodiment, a rectangular nesting block is formed from a mixture of vermiculite and expanded polystyrene beads. The vermiculite portion of the mixture is from 5 to 30%, preferably 10%. The block is molded with 2 to 4 bore holes in each square inch of area. The holes are of sufficient size for a leaf cutter bee to pass therethrough (approximately ¼ inch in diameter). The holes continue through the entire thickness of the rectangular block, which is approximately 3 inches. In operation, a porous backing sheet, such as paper or adhesive or screen, is placed on one side of the block so that the holes are accessible by the bees from one side only.

The blocks are placed in the field near an existing nesting area of leaf cutter bees and after eggs are layed therein, the blocks are removed from the field and placed in over winter storage.

The vermiculite mixture in the blocks allows air and some moisture to permeate throughout the block, thereby preventing mold from forming around the eggs or larvae.

DESCRIPTION OF THE DRAWINGS

The invention is more fully described in conjunction with the following drawings, wherein.

DETAILED DESCRIPTION

Figure 1:
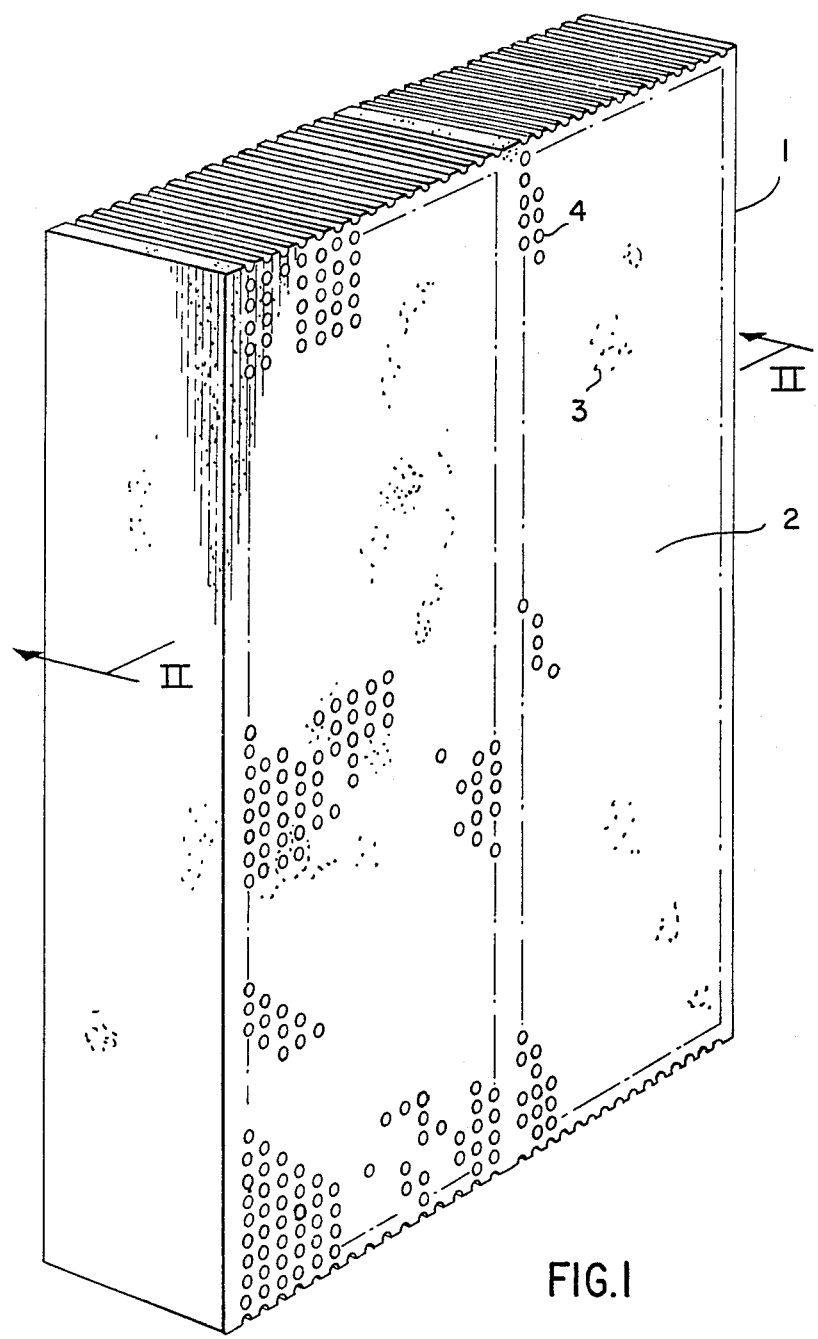
FIG. 1 is a perspective view of a nesting block of the present invention.

In FIG. 1, a nesting block 1 is comprised of EPS beads 2 and vermiculite 3. Bore holes 4 pass directly through the entire thickness of the nesting block 1.

Figure 2:
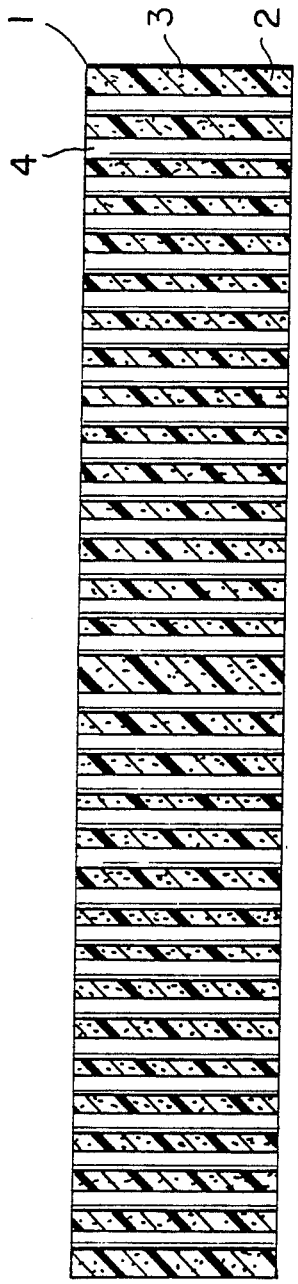
FIG. 2 is a cross-section II—II of FIG. 1.

In FIG. 2, the holes 4 are shown passing through the entire thickness of the nesting block 1.

Figure 3:
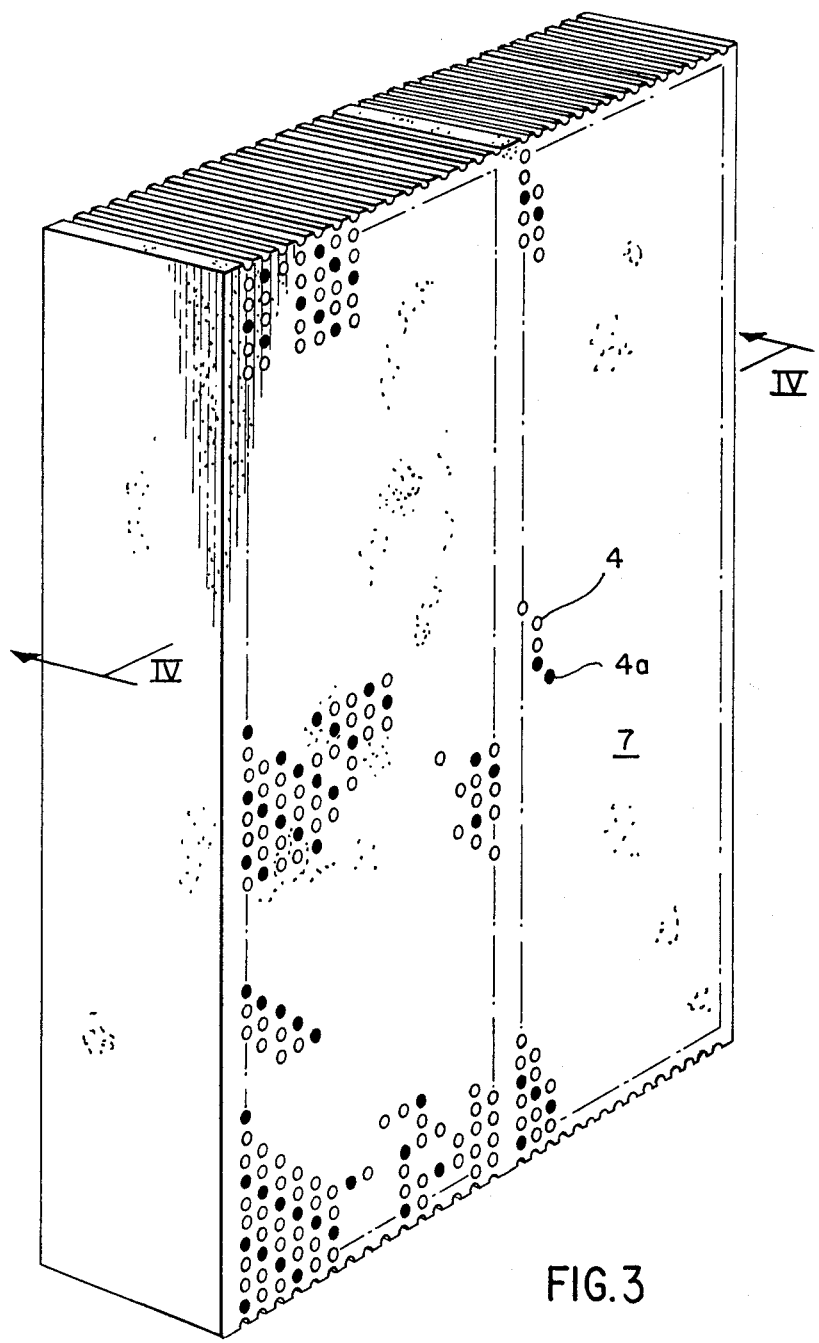
FIG. 3 is a perspective view of an alternate embodiment of the invention.

In FIG. 3, a number of the holes 4a are molded shut on side 7.

Figure 4:
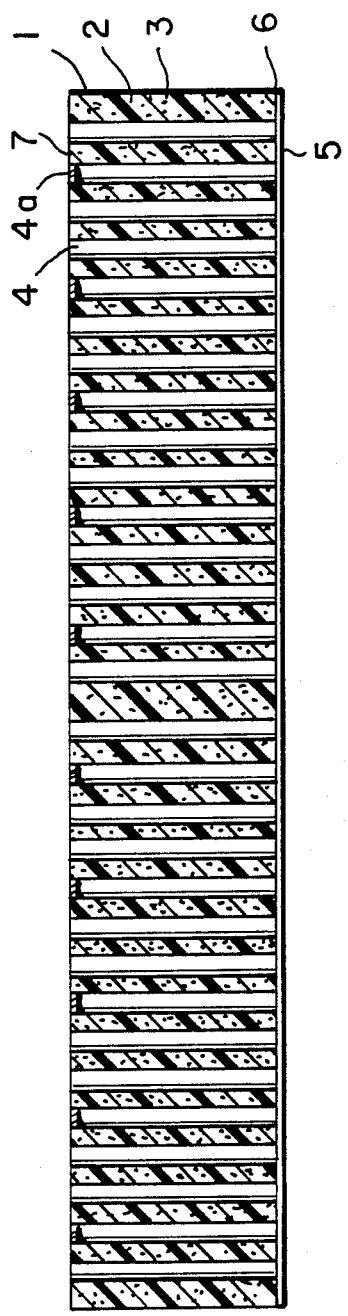
FIG. 4 is a cross-section IV—IV of FIG. 3.

In FIG. 4 an adhesive, porous, or other satisfactory backing sheet 5 is applied to the nesting block on one side 6 when the block is placed in the field in operation. When the backing sheet 5 is applied to this nest block, holes 4a are inaccessible to the bees while holes 4 are accessible only from side 7. Because of the vermiculite 3 within the block, moisture and air can travel throughout the block and the closed holes allow for greater permeability.

What I claim as my invention is:

1. A one piece molded nesting block for leaf cutting bees comprising:
    a mixture of polystyrene beads and 5% to 30% by weight of vermiculite; including a plurality of holes which pass through the entire thickness of said block and whereby when a backing sheet is applied to cover one side of said block in operation, said holes are accessible from one side only.

2. A one piece molded nesting block for leaf cutter bees comprising:
    a mixture of polystyrene beads and 5% to 30% by weight of vermiculite; including a first plurality of holes suitable for egg laying and development of larvae which pass through the entire thickness of said blocks; and a second group of holes wherein 5% to 50% said holes are blocked at one end wherein when in operation a backing sheet is applied to cover one side of said block, said first plurality of holes are accessible from one side only, and said second group of holes are inaccessible.

3. A one piece molded nesting block for leaf cutter bees comprising:
a mixture of polystyrene beads and approximately 10% by weight of vermiculite; including a plurality of holes which pass through the entire thickness of said block and are suitable for egg laying and development of larvae; whereby when in operation, a backing sheet is applied to cover one side of said block, said holes are accessible from one side only.

* * * * *